(12) United States Patent
Bühring

(10) Patent No.: US 6,323,321 B1
(45) Date of Patent: Nov. 27, 2001

(54) ANTIBODY 97A6

(75) Inventor: Hans-Jörg Bühring, Tübingen (DE)

(73) Assignee: Eberhard-Karls-Universitat Tubingen Universitatsklinikum (DE)

( * ) Notice: Subject to any disclaimer, the term of this patent is extended or adjusted under 35 U.S.C. 154(b) by 0 days.

(21) Appl. No.: 09/344,271

(22) Filed: Jun. 30, 1999

Related U.S. Application Data

(63) Continuation-in-part of application No. 09/031,386, filed on Feb. 26, 1998, now abandoned.

(30) Foreign Application Priority Data

Mar. 5, 1997 (DE) ................................................ 197 08 877

(51) Int. Cl.[7] ......................... A61K 39/395; C12N 5/20; G01N 33/574; G01N 33/577
(52) U.S. Cl. .................. 530/387.2; 424/93.1; 424/152.1; 424/130.1; 424/178.1; 424/184.1; 424/94.1; 424/85.1; 424/277.1; 435/4; 435/5; 435/7; 435/6; 435/7.1; 435/7.21; 435/14; 435/70.1; 435/46; 435/287; 435/325; 435/289; 436/500; 436/806; 436/95; 436/169; 436/120; 436/808; 436/805; 436/170; 436/119; 436/817; 436/291; 436/153.12; 530/387.1
(58) Field of Search ............................... 424/93.1, 152.1, 424/130.1, 178.1, 184.1, 94.1, 85.1, 277.1; 435/4, 5, 7, 6, 500, 7.1, 7.21, 14, 70.1, 46, 287, 289, 325; 436/291, 817, 153.12, 119, 120, 808, 169, 170, 805, 95, 806, 500; 530/387.1, 387.2

(56) References Cited

FOREIGN PATENT DOCUMENTS

06141852A * 5/1999 (JP) ............................... C12N/05/20

OTHER PUBLICATIONS

Harlow et al., "Labeling Antibodies", in, Antibodies: A Laboratory Manual. Chapter 9, pp. 319–3358, Jan. 1988.*

Komatsu et al., Establishment and Characterization of a humna Leukemic cell line., Cancer Research, 51, 341–348, Jan. 1, 1991.*

Yoshida et al., Studies on natral ST2 gene products in the humna leukemic cell line UT–7 using monoclonal antihuman st2 antibodies., Hybridoma, vol. 14, No. 5, 1995.*

Wu et al., Indentification of IgG Fc receptor type II on humna megakaryoblastic cell lines., British Journal of Haematology, 1993, 84 pp.204–211.*

Takafuta et al., Expression of platelet membrane glycoprotein V in humna magakaryocytes and megakayocytic cell lines., Thromb. Haemostasis., 1994, 72(5), 762–769.*

Van den Oudenrijn et al., "Reactivity of the blind monoclonal antibody panel of the platelet section with megakaryocytic cell lines and cultured CD34 cells" Tissue Antigens–6th International workshop and conference on human leukocyte differentiation anti, Nov. 1996.*

Van Den Oudenrijn S. et al., "Reactivity of the Blind Monoclonal Antibody Panel of the Platelet Section With Megakaryocytic Cell Lines and Cultured CD34+Cells" *Tissue Antigens–6th International Workshop and Conference on Human Leukocyte Differentiation Antigens*, Bd. 48, Nr. 4–2, 10.—(Nov. 14, 1996) Kobe Japan.

Winderbank K. et al., Acute Megakaryocytic Leukemia (M7) in Childred, *Mayo Clinical Proceedings*, Bd. 64, Nr. 11, (1989) Seiten 1339–1351.

* cited by examiner

*Primary Examiner*—Christopher L. Chin
*Assistant Examiner*—Lisa V. Cook
(74) *Attorney, Agent, or Firm*—Oppenheimer Wolff & Donnelly LLP; Claude A. S. Hamrick

(57) ABSTRACT

The present invention relates to a monoclonal antibody binding an antigen on the megakaryocytic cell line UT-7. The invention further relates to hybridoma cells producing such an antibody.

8 Claims, 2 Drawing Sheets

UT-7

97A6

CD117

CD13

CD33

CD41

CD61

CD109

UT-7/97A6

97A6

CD117

CD13

CD33

CD41

CD61

CD109

ANTIBODY 97A6

CROSS REFERENCE TO RELATED APPLICATIONS

This application is a continuation-in-part of application Ser. No. 09/031,386 filed on Feb. 26, 1998, now abandoned, which is a conterpart U.S. application to German application No. 197,088,77.5 filed in Federal Republic of Germany on Mar. 5, 1997.

BACKGROUND OF THE INVENTION

1. Field of the Invention

The invention relates to a monoclonal antibody which binds to an antigen on the megakaryocytic cell line UT-7.

Antibodies of this kind are generally known.

2. Description of the Related Art

Until now, diagnostic analyses have been carried out either microscopically according to cell morphology after staining with classical staining methods, for example staining according to Pappenheim, and by manually counting. In modern methods for analysis of bone marrow biopsies or blood samples antibodies detecting specific antigens as markers for specific cell types and cell stages are used. The recognized antigens can be detected automatically using standard methods like EEISA (enzyme linked immunosorbent assay) or flow cytometry (FACS analysis, fluorescence activated cell sorting) in an automatic manner. Adequate antibodies having a high sensitivity and above all specificity for the different cell types and cell stages and additionally being available in large amounts are essential for the application of these kinds of methods.

SUMMARY OF THE INVENTION

It is, therefore, an object of the present invention to provide an antibody detecting an antigen on the megakaryocytic cell line UT-7 and being available in practically unlimited amounts.

The object is achieved by providing a monoclonal antibody produced and released by hybridoma cells deposited under No. DSM ACC2297 on Feb. 12, 1997, at "Deutsche Sammlung von Mikroorganismen und Zellkulturen GmbH (DSMZ)", the German Collection of Microorganisms and Cell Cultures Ltd. Mascheroder Weg 1b, D-38124 Braunschweig, Germany, under the provision of the Budapest Treaty, that all restrictions upon public access to the deposit will be irrevocably removed upon the grant of a patent on this application and that the deposit will be replaced if viable samples cannot be dispensed by the depository. The antibody is designated 97A6.

The invention also relates to hybridoma cells that have been deposited under No. DSM ACC2297 at "Deutsche Sammlung von Mikroorganismen und Zellkulturen GmbH (DSMZ)", the German Collection of Microorganisms and Cell Cultures Ltd., Mascheroder Weg 1b, D-38124 Braunschweig, Germany, under the provision of the Budapest Treaty, that all restrictions upon public access to the deposit will be irrevocably removed upon the grant of a patent on this application and that the deposit will be replaced if viable samples cannot be dispensed by the depository producing the antibody having the designation 97A6.

In order to facilitate the application of the antibody according to the invention, the antibody can be mixed with adequate auxiliary substances in a pharmaceutical composition. Consequently, the invention also relates to a pharmaceutical agent, comprising the antibody according to the invention. Preferably, this pharmaceutical agent comprises the antibody produced and secreted by hybridoma cells deposited under No. DSM ACC2297 at the "Deutsche Sammlung von Mikroorganismen und Zellkulturen GmbH, DSMZ", the German Collection of Microorganisms and Cell Cultures Ltd.

In an especially preferred version of the pharmaceutical agent the antibody is linked to a marker, especially to a fluorescent marker.

It is advantageous that the antibody can be detected with a high sensitivity and therefore only small amounts of the pharmaceutical means have to be applied for diagnosis. Additionally, the application of a pharmaceutical agent of this kind renders the diagnosis by means of automatic ELISA readers and flow cytometers possible.

Further advantages can be taken from the following description.

It is understood that the afore-mentioned features and those to be explained in the following can be used not only in the specific combination, but also in other combinations or alone without going beyond the scope of the present invention.

BRIEF DESCRIPTION OF THE DRAWINGS

The invention will be described hereafter with reference to certain exemplified applications and embodiments in combination with the drawings.

DETAILED DESCRIPTION OF PREFERRED EMBODIMENTS OF THE INVENTION

EXAMPLE 1

Figure 1:
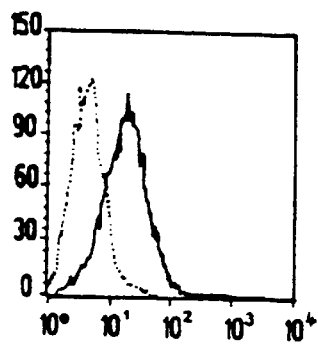
FIG. 1 shows seven histograms of flow cytometric measurements regarding the expression of seven different cell surface structures of the cell line UT-7.
Figure 1:
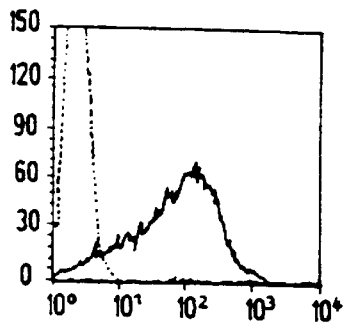
Figure 1:
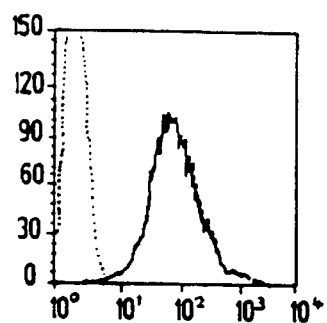
Figure 1:
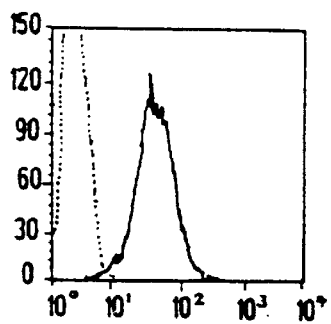
Figure 1:
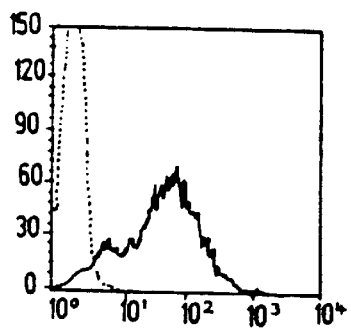
Figure 1:
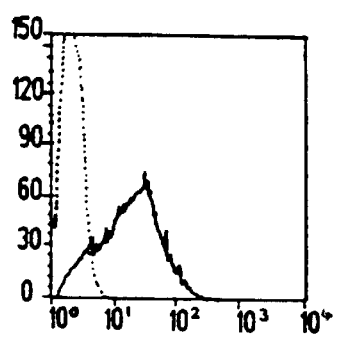
Figure 1:
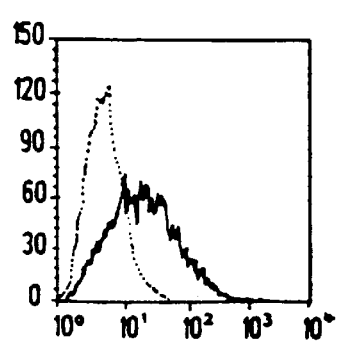

Establishment and Characterization of Monoclonal Antibodies Which Bind to An Antigen on the Megakaryocytic Cell Line UT-7

Cells of the erythro-/megakaryoblastic cell line UT-7 were used as the antigen (Komatsu N. et al., Establishment of a human leukemic cell line with megakaryocytic features: Dependency on granulocyte-macrophage colony-stimulating factor, interleukin-3, or erythropoetin for growth and survival, Cancer Res. 1991; 51: 341–348).

Eight week old Balb/c mice are immunized intraperitonially twice at intervals of ten days, with $10^7$ cells of the cell line UT-7. Four days before the fusion, $5 \times 10^5$ cells are administered directly into the spleen in order to reinforce the immune response.

The formation of antibodies in the organism of the mouse is tested by screening the blood serum of the respective animal for binding properties to the antigen using the ELISA test well-known to the person skilled in the art.

Approximately three weeks later the lymphocytes of the successfully immunized animal are collected by removing the animal's spleen and homogenizing it into a cell suspension. The suspended spleen cells are fused with myeloma cells of the known strain SP2/0 in the presence of polyethylene glycol. The fusion culture is cultivated in a medium containing hypoxanthine, aminopterin and thymidine (HAT), here in HAT-RPMI-1640, in which only hybrid cells can grow since these have both the property of myeloma cells to divide infinitely, and the property of the antibody producing lymphocytes to grow in a medium containing HAT.

Following fusion, the cells are plated into microliter plates and are incubated at 37° C. in the presence of 5% $CO_2$.

The culture supernatants are screened in a flow cytometer after 10–14 days using the cell line UT-7. In a second step, the supernatants are tested for reactivity with peripheral blood cells, to sort out those hybridoma cells, producing antibodies not selected for bone marrow cell antigens. Supernatants showing a negative or weak reaction with peripheral blood cells are subsequently selected and isolated, i.e. cloned, using the limited dilution method known in the art.

Positively reacting hybridoma cell cultures are further cultivated and the antibodies are concentrated, purified and characterized.

The monoclonal antibody 97A6 was obtained by the screening strategy described above. The isotype was determined to be IgG1 using PE-conjugated anti-isotype-specific antisera, by direct immune fluorescence.

Production, purification and characterization of the antibody were carried out using methods generally known in the art. The antibody 97A6, produced by the hybridoma cells deposited under No. DSM ACC2297 at the "Deutsche Sammlung von Mikroorganismen und Zellkulturen GmbH, DSMZ", the German Collection of Microorganisms and Cell Cultures Ltd., has the following features:

Immunoglobulin class: IgG1

Binding affinity to: an antigen expressed on the d on the surface of the megakaryocytic cell 4line UT-7 line, UT-7

EXAMPLE 2

Screening of Established Cell Lines for Detection by Antibody 97A6

For analysis of the specificity of the antibody 97A6 48 different established cell lines were analyzed for reactivity with the antibody 97A6. The results are listed below in table 1.

The derivation as well as the essential features of each single cell line were known, so that this experiment does not only elucidate the specificity of the antibody but also provides information about the expression of the 97A6 antigen so far not characterized.

The reaction of the cells with the antibody 97A6 was measured in the flow cytometer (FACS).

TABLE 1

| Reaction of antibody 97A6 with various cell lines | | | |
|---|---|---|---|
| Cell line | Type of cell line | Features of cell line | Detection by 97A6 |
| DU.4475 | tumor cell line | breast carcinoma (epithelial) | – |
| T-47D | tumor cell line | breast carcinoma | – |
| MCF-7 | tumor cell line | breast carcinoma | – |
| NCI-H128 | tumor cell line | SCLC (Small Cell Lung Cancer) | – |
| NCI-H69 | tumor cell line | SCLC (Small Cell Lung Cancer) | – |
| SK-MES | tumor cell line | lung carcinoma (squamous) | – |
| Calu 1 | tumor cell line | lung carcinoma (epidermoid) | – |
| Calu 3 | tumor cell line | lung carcinoma (adeno) | – |
| Calu 6 | tumor cell line | lung carcinoma (adeno) | – |
| SK-LU1 | tumor cell line | lung carcinoma (adeno) | – |
| HELA | tumor cell line | cervix carcinoma (epithelial) | – |
| 5637 | tumor cell line | bladder carcinoma (epithelial-like) | – |
| IMR-32 | tumor cell line | neuroblastoma (fibroblast and neuroblast-like | – |
| TE-671 | tumor cell line | medulloblastoma (epithelial-like) | – |
| A172 | tumor cell line | glioblastoma | – |
| U138 | tumor cell line | glioblastoma | – |
| U373 | tumor cell line | glioblastoma | – |
| A431 | tumor cell line | epidermal carcinoma | – |
| MKPL1 | leukemic cell line: erythroblast/megakaryocytic | megakaryoblastic leukemia | + |
| KU.812 | leukemic cell line: erythroblast/megakaryocytic | megakaryocytic/ basophil leukemia Ph+* (CML)** | + |
| UT-7 | leukemic cell line: erythroblast/megakaryocytic | erythro-/megakaryocytic leukemia | + |
| TF-1 | leukemic cell line: erythroblast/megakaryocytic | erythro-/megakaryocytic leukemia | – |
| M07e | leukemic cell line: erythroblast/megakaryocytic | erythro-/megakaryocytic leukemia | – |
| MEG-01 | leukemic cell line: erythroblast/megakaryocytic | erythro-/megakaryocytic leukemia Ph+* (CML)** | + |
| MOLM-1 | leukemic cell line: erythroblast/megakaryocytic | erythro-/megakaryocytic leukemia Ph+* (CML)** | – |
| K562 | leukemic cell line: erythroblast/megakaryocytic | erythro-/megakaryocytic leukeimia Ph+* (CML)** | – |
| HEL | leukemic cell line: erythroblast/megakaryocytic | erythro-/megakaryocytic leukemia Ph+* (CML)** | – |
| EM2 | leukemic cell line: myeloblastic | myeloblastic, Ph+* (CML)** | – |
| KG-1 | leukemic cell line: myeloblastic | myeloblastic leukemia | – |
| KG-1a | leukemic cell line: myeloblastic | immature subline of KG-1 | – |
| HL60 | leukemic cell line: | myeloblastic leukemia | – |

TABLE 1-continued

Reaction of antibody 97A6 with various cell lines

| Cell line | Type of cell line | Features of cell line | Detection by 97A6 |
|---|---|---|---|
| DU.528 | myeloblastic leukemic cell line: | myeloblastic leukemia | – |
| U937 | myeloblastic leukemic cell line: | myeloblastic leukemia | – |
| OCI/AML-4 | myeloblastic leukemic cell line: | myeloblastic leukemia | – |
| CML-T1 | myeloblastic leukemic cell line: | T-lymphoblastic Ph+* (CML)** | – |
| HSB-2 | T-lymphoblastic leukemic cell line: | T-lymphoblastic leukemia | – |
| CCRF-CEM | T-lymphoblastic leukemic cell line: | T-lymphoblastic leukemia | – |
| Molt-4 | T-lymphoblastic leukemic cell line: | T-lymphoblastic leukemia | – |
| Jurkat | T-lymphoblastic leukemic cell line: | T-lymphoblastic leukemia | – |
| Daudi | T-lymphoblastic leukemic cell line: | EBV transformed cell line | – |
| Reh | B-lymphoblastic leukemia cell line: | pre-B-lymphoblastic leukemia | – |
| 207 | B-lymphoblastic leukemia cell line: | pre-B-lymphoblastic leukemia | – |
| 380 | B-lymphoblastic leukemia cell line: | pre-B-lymphoblastic leukemia | – |
| 697 | B-lymphoblastic leukemia cell line: | pre-B-lymphoblastic leukemia | – |
| Km3 | B-lymphoblastic leukemia cell line: | pre-B-lymphoblastic leukemia | – |
| BV-173 | B-lymphoblastic leukemia cell line: | pro-B-lymphoblastic Ph+* (CML)**, (CD10+) | – |
| Nalm-1 | B-lymphoblastic leukemia cell line: | pre-B-lymphoblastic Ph+* (CML)**, (CD10+) | – |
| U266 | leukemia cell line: B-lymphoblastic | myeloma cell line | – |

*Ph+ means Philadelphia Chromosome positive
**CML means chronic myeloid leukemia

EXAMPLE 3

Analysis of the Binding of Various Monoclonal Antibodies to Megakaryocytic Cell Lines In connection with a cluster workshop a total of 14 different monoclonal antibodies were tested for their reactivity with different megakaryocytic cell lines by means of flow cytometry. One of the antibodies tested was the antibody 97A6, which was called P50 in this study. The antibody was made available by the inventor in connection with the "VI International Workshop and Conference on Human Leukocyte Differentiation Antigenes, Japan, 1996". At this workshop panels of antibodies were given to an investigator assisting in clustering only for experimental testing but antibodies never were publicly available.

According to the "Conditions for Participation" of this "cluster workshop" each workshop section has to aliquot the antibodies submitted by a party and provide panels to investigators who are acting as reference laboratories, assisting in the clustering. The results of the experiments have to be reported at the meeting prior to communication elsewhere. Monoclonal antibodies cannot be used for cloning without the specific prior consent of the submitter of the antibody. The inventor of this application has not given his consent to using the antibody 97A6 for a purpose other than clustering antigens.

According to the present state of the art the established cell lines employed in this experiment represent different differentiation stages of the megakaryocytic development from undifferentiated stem cells (CD34+-cells, cell line KGla) to thrombocytes. The analyses are taken from the publication of Sonja van den Oudenrijn et al.: Reactivity of the blind monoclonal antibody panel of the platelet section with megakaryocytic cell lines and cultured CD 34+ cells. In: Leukocyte Typing VI, Kishimoto T. et al., eds. Garland Publishing, Inc. New York (1997), presenting results of experiments done in connection with the workshop and under the above-mentioned "Conditions". The results are given in table 2.

TABLE 2

Reaction of various antibodies with megakaryocytic cell lines

| employed antibodies | tested cell lines | | | | | | |
|---|---|---|---|---|---|---|---|
| | KG1a | K562 | HEL | CHRF | MKPL | MEGO | thrombocytes |
| CD41 (6C9) | 32 | — | 16 | 74 | 90 | 51 | 99 |
| CD42b (MB45) | — | 13 | — | 10 | 11 | — | 98 |
| CD63 (435) | 98 | 94 | 78 | 36 | 94 | 79 | 14 |
| P48 (11B2.G4) | 100 | 94 | 93 | 94 | 96 | 85 | 95 |
| P49 (14A2.H1) | 96 | 80 | 30 | 25 | 81 | 53 | 86 |

TABLE 2-continued

Reaction of various antibodies with megakaryocytic cell lines

| employed antibodies | tested cell lines | | | | | | |
|---|---|---|---|---|---|---|---|
| | KG1a | K562 | HEL | CHRF | MKPL | MEGO | thrombocytes |
| P50 (97A6) | — | — | — | — | 81 | 66 | — |
| P51 (Ad2/13H12) | 12 | — | — | — | — | 22 | 19 |
| P52 (ALMA.7) | — | — | — | — | — | — | 91 |
| P53 (HIP10) | 35 | 42 | 39 | 76 | 78 | 56 | 94 |
| P54 (HIP11) | 27 | — | 15 | 68 | 74 | 50 | 97 |
| P55 (NaM12-6B6) | — | — | — | — | — | — | 94 |
| P56 (NaM28-8C12) | — | — | 18 | — | 87 | 16 | 94 |
| P57 (NaM81-1D10) | — | — | — | — | — | — | 23 |
| P58 (UM.8D2) | 98 | 88 | 96 | 99 | 87 | 63 | 62 |

The reactivities of the antibodies are given as the percentage of positive cells, and a minus represents a non-specific binding of less than 10%.

EXAMPLE 4

Generation of a Subline of UT-7 Having a High Expression of 97A6 Antigen

So far neither structure nor function of the 97A6 specific antigen are known.

Since whole cells of the cell line UT-7 were used for immunization during generation of the hybridoma cell line producing the monoclonal antibody 97A6, the respective antigen is supposed to be a membrane bound cell surface protein of this cell line.

Additionally, the antigen is expressed in three further cell lines, including cell line MKPL1 (see example 1). For identification of the respective gene an overexpressing cell line was generated for generation of an expression library. UT-7 cells were incubated with the antibody 97A6 and a fluorescence labeled second antibody. 5% of the cells having the highest density of antigen were then selected by means of a FACSVantage cell sorter.

Figure 2:
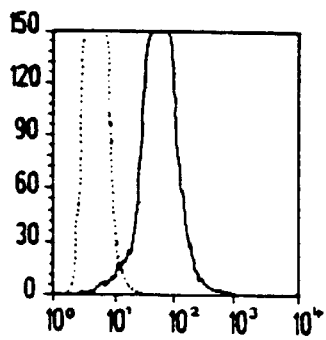
FIG. 2 shows histograms of the flow cytometric measurements of the same seven cell surface structures as in FIG. 2, but obtained with a subline of UT-7 having a high expression of the 97A6 antigen.
Figure 2:
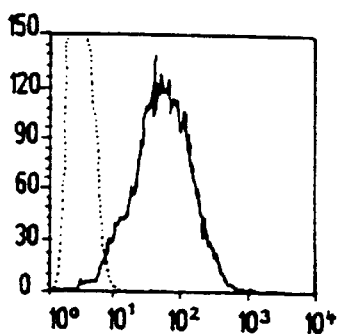
Figure 2:
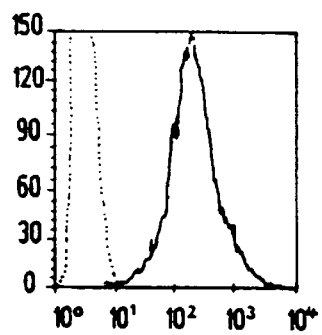
Figure 2:
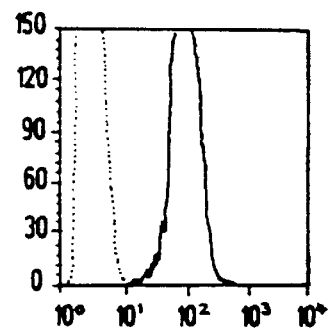
Figure 2:
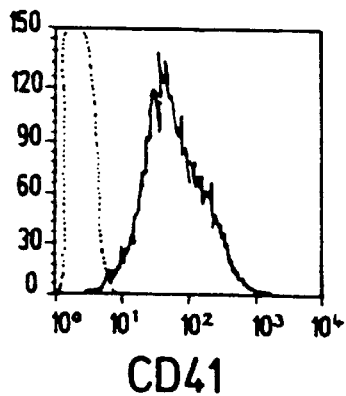
Figure 2:
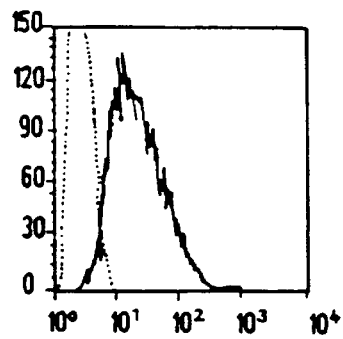
Figure 2:
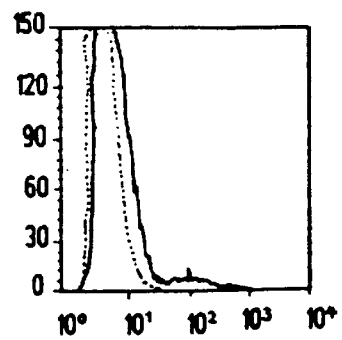

These cells were grown in culture and the process was repeated after having obtained 10⁷ cells. The resulting cell line was called UT-7/97A6. FIGS. 1 and 2 show the results of the flow cytometric analysis of cell lines UT-7 and UT-7/97A6. The degree of expression of the 97A6 specific antigen as well as the expression of additional six antigens in the original cell line UT-7 (FIG. 1) and the selected cell line UT-7/97A6 (FIG. 2) is shown. The intensities of fluorescence resulting from the histograms of the FACS analysis are summarized in table 3, representing the expression rate of the antigens.

TABLE 3

Expression of different antigens on UT-7 and UT-97A6

| analyzed antigen | type of marker | mean intensity of fluorescence on UT-7 | mean intensity of fluorescence on UT-7/97A6 |
|---|---|---|---|
| 97A6 specific antigen | | 26,44 | 67,14 |
| CD117 | stem cell marker | 128,9 | 77,02 |
| CD109 | stem cell marker | 29,3 | 9,36 |
| CD13 | myeloic marker | 144,61 | 291,73 |
| CD33 | myeloic marker | 42,28 | 103,35 |
| CD41 | megakaryocytic marker | 70,61 | 100,54 |
| CD61 | megakaryocytic marker | 25,8 | 33,9 |

These results show that the subline of cell line UT-7 isolated using the antibody 97A6 expresses approximately three times more of the 97A6 specific antigen as compared to the original cell line. The cell line UT-7/97A6 further comprises features typical for a megakaryocytic cell in an advanced differentiation stage. The expression rate of stem cell markers CD117 and CD109 is substantially diminished in the sub cell line as compared to the original cell line, while the expression of the myeloid markers CD13 and CD33 as well as the megakaryocytic markers CD41 and CD61 are expressed in higher amounts in the generated subline. The cell line UT-7/97A6 therefore represents a more mature cell line as compared to the original cell line.

The cell line serves as the basis for generation of an expression library from which the coding sequence for the antigen can be isolated.

The nucleic acid or amino acid sequence will then elucidate the nature and possibly also the function of the 97A6 antigen.

Therefore, what I claim, is:

1. A monoclonal antibody which binds to an antigen on the megakaryocytic cell line UT-7, produced and released by hybridoma cells deposited on Feb. 12, 1997 at the International Depository DSMZ, German Collection of Microorganisms and Cell Cultures Ltd., Mascheroder Weg 1b, D-38124 Braunschweig, Germany, under No. DSM ACC2297, in accordance with the Budapest Agreement, the antibody having the designation 97A6 or P50.

2. Hybridoma cells deposited on Feb. 12, 1997 at the International Depository DSMZ, German Collection of Microorganisms and Cell Cultures Ltd., Mascheroder Weg 1b, D-38124 Braunschweig, Germany, under No. DSM ACC2297, in accordance with the Budapest Agreement.

3. The monoclonal antibody according to claim 1, linked to a detectable marker.

4. The monoclonal antibody according to claim 3, wherein the marker is a fluorescent marker.

5. A composition comprising the antibody according to claim 1.

6. A composition comprising the antibody according to claim 3.

7. The composition of claim 5, further comprising a pharmaceutically acceptable carrier.

8. The composition of claim 6, further comprising a pharmaceutically acceptable carrier.

* * * * *